（12) United States Patent
Castignoles et al.

(10) Patent No.: US 12,186,180 B2
(45) Date of Patent: Jan. 7, 2025

(54) DIFFRACTIVE OCULAR IMPLANT WITH ENLARGED NEAR VISION

(71) Applicant: Cristalens Industrie, Lannion (FR)

(72) Inventors: Fannie Castignoles, Tredrez Locquemeau (FR); Laure Gobin, Ville d'Avray (FR); Denis Delage, Dinge (FR)

(73) Assignee: Cristalens Industrie (FR)

( * ) Notice: Subject to any disclaimer, the term of this patent is extended or adjusted under 35 U.S.C. 154(b) by 419 days.

(21) Appl. No.: 17/627,175

(22) PCT Filed: Jul. 13, 2020

(86) PCT No.: PCT/EP2020/069763
§ 371 (c)(1),
(2) Date: Jan. 14, 2022

(87) PCT Pub. No.: WO2021/009125
PCT Pub. Date: Jan. 21, 2021

(65) Prior Publication Data
US 2022/0265419 A1   Aug. 25, 2022

(30) Foreign Application Priority Data
Jul. 17, 2019   (FR) ...................................... 1908077
Jul. 2, 2020    (FR) ...................................... 2007000

(51) Int. Cl.
*A61F 2/16*   (2006.01)

(52) U.S. Cl.
CPC ................................. *A61F 2/1654* (2013.01)

(58) Field of Classification Search
None
See application file for complete search history.

(56) References Cited

U.S. PATENT DOCUMENTS

2007/0182921 A1   8/2007   Zhang et al.
2020/0281715 A1   9/2020   Castignoles et al.

FOREIGN PATENT DOCUMENTS

FR        3072020 A1    4/2019
WO        03107076 A1   12/2003

OTHER PUBLICATIONS

International Search Report for PCT/EP2020/069763 dated Oct. 14, 2020. 4 pgs.

*Primary Examiner* — Javier G Blanco
(74) *Attorney, Agent, or Firm* — Lerner David LLP

(57) ABSTRACT

The present invention relates to a diffractive ocular implant with correct distance vision and enlarged near vision, which is charaterised, in particular, in that it has a phase-transfer curve as a function of the viewing distance (abbreviated as PTFF-TF) with an absence of discontinuity over a depth of field of at least 1.3D in corneal plane, advantageously greater than 1.45D, the absence of discontinuity being located between intermediate vision and near vision, i.e., between 0.5D and 4D for spatial frequencies from 0 to 100 cycles/mm, for a pupil with a diameter of at least 3 mm.

12 Claims, 8 Drawing Sheets

DIFFRACTIVE OCULAR IMPLANT WITH ENLARGED NEAR VISION

CROSS-REFERENCE TO RELATED APPLICATIONS

The present application is a national phase entry under 35 U.S.C. Å 371 of International Application No. PCT/EP2020/069763 filed Jul. 13, 2020, which claims priority from French Application Nos. 2007000 filed Jul. 2, 2020, and 1908077, filed Jul. 17, 2019, all of which are hereby incorporated herein by reference.

FIELD OF THE INVENTION

The present invention belongs to the field of ocular implants.

It more particularly relates to a diffractive ocular implant with enlarged near vision.

TECHNOLOGICAL BACKGROUND OF THE INVENTION

Cataract is the loss of transparency of the natural lens. The natural lens contributes a third of the light convergence in the eye. Cataract surgery consists of removing the natural lens to restore sharp vision. In the 1950s, Mr. Ridley implanted the first intraocular lenses in the sulcus to correct aphakia and thus restore the missing third of optical power. Intraocular lenses are now implanted in the capsular bag.

With no accommodation (at rest), objects located at a distance are focused (clear) on the retina of an emmetropic eye (neither myopic, nor hyperopic, nor astigmatic).

In order to clearly see near objects (from intermediate to near distance), the young natural lens has the ability to change shape. Thus, by the action of the ciliary muscles which relax the zonular fibers by contracting, the anterior and posterior radii of curvature of the natural lens increase its optical power by several diopters.

The loss of this accommodation comes with age and appears in all cases after cataract surgery during which the natural lens is replaced by an artificial lens that does not have the ability to change its power according to the desired viewing distance.

Some so-called accommodating implants (deformable polymers, moving optics) try to restore accommodation, but the results are not currently satisfactory (in part because of fibrosis of the capsular bag which, over time, limits the possibilities for changing shape).

To alleviate this loss of accommodation, many multifocal implants have been developed. They are based on the division of light energy over several vision zones. At the start of the 2000s, diffractive optics proved their superiority in distance and near vision relative to refractive optics.

Diffractive optics allow many choices for distribution of diffraction energy according to the chosen viewing distances. The optical quality resulting from the chosen profile is defined by its MTF (modulation transfer function).

The MTF is a number comprised between 0 and 1 (or 0% and 100%) which represents the image contrast (the image can be non-contrasted because it is defocused or because the energy is shared among several focal points). "Through focus" MTF, abbreviated MTF-TF, represents the MTF as a function of defocusing (which is represented either as a function of the viewing distance or as a function of the addition (1 D=1/1 m)) MTF-TF makes it possible to determine the depth of field.

The literature has shown that regardless of the optical profile or technology, the visual results are related to the MTF profile of the intraocular lens (IOL) or implant implanted. Thus, on average, binocular visual acuity is better than:

0 LogMAR (10/10) when the MTF is 0.40;
between 0 and 0.05 LogMAR (9/10) for an MTF of 0.20;
0.1 LogMAR (8/10 for an MTF of 0.15,
when the MTF is at 3 mm and at 50 cycles/mm, MAR meaning "minimum angle resolution".

The first diffractive optics were bifocal optics with one MTF peak for distance vision (addition OD) and an other peak for near vision (+3 D or +4 D addition). These implants allow sharp vision for reading (at around 40 cm) but patients must wear correction for intermediate vision (between 40 and 90 cm).

In order to get closer to ideal vision (without correction by eyeglasses), with sharp and continuous vision at all distances of near vision (from 40 to 90 cm), several solutions have been developed:

Mix Et Match;
"EDOFs";
trifocal implants
Mix Et Match:

Mix and Match consists of using two bifocal implants with different additions for each eye (one eye for near vision, the other for intermediate vision).

The goal is to provide a contrasted image in intermediate vision, which is not the case for trifocal implants. Combinations of +1.75 D/+4 D and +1.5 D/+3 D (IOL plane additions) have given interesting defocus curves (i.e., visual acuity as a function of viewing distance). But the limit of this solution is the patient's binocular vision comfort. In order to preserve a binocular balance, an addition difference of 0.5 D has been proposed and the +2.5 D/+3 D combination (IOL plane additions) has shown results similar to trifocals, except in the 1 D and 1.5 D zone (in the corneal plane).

EDOFs (Abbreviation for "Extended Depth of Focus" or "Extended Depth of Field")

Extended depth of field implants are bifocal (or sometimes trifocal) implants with lower additions to allow good intermediate vision. Note that the lower the addition, the greater its distance depth of field will be because addition is a "1/x" function of distance. These implants provide comfort for computer vision (intermediate vision), but it is necessary to wear corrective glasses for near vision.

Trifocal Implants

Trifocal implants are diffractive IOLs whose energy is distributed over 3 vision peaks, i.e. distance, intermediate and near. They therefore allow sharp vision and intermediate vision where bifocal implants only have sharp near vision. Currently, trifocal implants are the most advanced "top of the line" solution to achieve a sharp vision from infinity to near.

But trifocal implants have three distinct vision peaks with a contrast discontinuity, of the MTF-TF between near vision and intermediate vision. In some trifocal implants, this discontinuity is visible on the MTF-TF at 50 cycles/mm, which represents the intermediate letter size. Vision is therefore sharp at 40 and 80 cm, but not at 60 cm.

In other implants, this MTF-TF discontinuity is found at 100 cycles/mm, i.e., for smaller letter sizes.

The prior art of interest relative to the present invention consists of the documents FR 3 072 020, US 2007/182921 and WO 03/107076.

The objective of the present invention is to alleviate the disadvantages indicated above and to offer an intraocular implant that makes it possible to obtain sharp and continuous vision over the entire useful near vision zone and requiring the smallest characters to be deciphered (reading a book positioned 40 cm from the reader, mobile phone, tablet, laptop computer placed 60 cm from the user, stationary computer placed 80 cm etc.).

SUMMARY OF THE INVENTION

Thus, the present invention relates to a diffractive ocular implant with correct distance vision and enlarged near vision, characterized by the fact that it has a phase transfer curve as a function of the viewing distance (abbreviated PTF-TF) with an absence of discontinuity over a depth of field of at least 1.3 D in the corneal plane, i.e., over an area of additions in the corneal plane of at least 1.3 D, the addition in the corneal plane being understood as the inverse of the distance between the object viewed and the cornea, advantageously greater than 1.45 D, which absence of discontinuity is located between intermediate vision and near vision, i.e. between 0.5 D and 4 D for spatial frequencies from 0 to 100 cycles/mm for a pupil of at least 3 mm in diameter and which comprises a body with at least one optical surface having an optical axis and a plurality of diffractive zones arranged concentrically around said optical axis, these concentric zones each having at least one radius r and being distributed between a central region and a peripheral region, this implant being noteworthy in that at least one central or peripheral region of the said diffractive zones has a profile of N successive echelettes, the successive radii of which, as one moves away from the said optical axis, respond to the relation:

$$r_N = \sqrt{2N\lambda f_p^2 \cdot \lambda F2(N) \cdot \Delta_f}$$

relation wherein:
N is a whole number greater than 1;
$\lambda$ is the conception wavelength;
fp is the focal length corresponding to the addition for near vision;
$\Delta f$ is the focal length variation, which is non-zero, positive or negative, and whose absolute value is less than 10,000;
F2(N) is either a polynomial of the variable N of at least order 3, preferably 3 to 5, which is expressed as follows:

$$F2(N) = cte + a \cdot N + b \cdot N^2 + c \cdot N^3 + d \cdot N^4 + \ldots,$$

or a function whose limited development or Taylor is equivalent to the polynomial expressed above.
height h of said successive echelettes (diffractive steps) being given by the relation:

$$h = \alpha \frac{\lambda}{\Delta n}$$

relation wherein:
$\Delta n$ is the refractive index variation, i.e., the difference between the refractive index of the implant material and that of the aqueous humor of the eye or the surrounding environment;
$\alpha$ is the height factor of the echelette, comprised between 0.25 and 1.75.

Thanks to the invention, near vision depth of field is gained while conserving good distance vision, with no discontinuity up to spatial frequencies of 100 cycles/mm.

The expression "at least of order 3" indicates the minimum order of the polynomial. It is particularly inappropriate to define a maximum order. Indeed, for example, an equation of order 10 can be considered, but with a preponderant order 3 and negligible coefficients on order 10.

According to other non-limiting and advantageous characteristics of the invention, taken alone or according to any combination of at least two of these:
cte is a real number comprised between −5 and +5,
a, b, c, d, etc. are real numbers comprised between −5 and +5,
said diffractive zones have a circular contour;
said diffractive zones have an elliptical contour of which $r_N$ is the small radius;
said diffractive zones are made up by alternating full zones and empty zones, these latter especially consisting of slits or holes or by local changes in the refractive index.
said curve has no discontinuity from 0.8 D in the corneal plane;
said curve has no discontinuity from 2 D in the corneal plane;
said region is a central region which has a radius of at least one millimeter and which is surrounded by a peripheral region which is refractive or diffractive, monofocal or multifocal, for example with a bifocal equation:

$$r_N = \sqrt{2N\lambda \cdot f_p};$$

said region is a peripheral region, which surrounds a central region, the latter having a radius of at least one millimeter and being refractive or diffractive, monofocal or multifocal, for example with a bifocal equation:

$$r_N = \sqrt{2N\lambda \cdot f_p};$$

function F2(N) a polynomial of the variable N of order 3;
the implant is chosen in the following group: intracorneal implant, anterior chamber (phakic or pseudophakic), posterior intraocular chamber or sulcus implant;
it has an aspherical surface;
It has an apodized profile, i.e., the height of said echelettes decreases as one moves away from said optical axis, in order to limit the halo phenomenon in night vision.

Throughout the present application, the expression "correct distance vision" means vision such that the MTF is greater than 20% at 50 cycles/mm in a 3-mm pupil.

The expression "enlarged near vision" is defined by the formulation "characterized by the fact that it has a phase transfer curve as a function of the viewing distance (abbreviated PTF-TF) with an absence of discontinuity over a depth of field of at least 1.3 D in the corneal plane, i.e., over an area of additions in the corneal plane of at least 1.3 D, the addition in the corneal plane being understood as the inverse of the distance between the object viewed and the cornea, advantageously greater than 1.45 D".

BRIEF DESCRIPTION OF THE DRAWINGS

Other characteristics and advantages of the invention will appear upon reading the following description of embodiments of the invention. This description is made in reference to the attached drawings in which.

DETAILED DESCRIPTION OF THE INVENTION

Throughout the following, unless otherwise stated, addition is indicated in the corneal plane.

Concept of Phase Transfer Function (PTF)

Any optical system can be represented by its point spread function (PSF).

PSF is the spatial distribution of light intensity in the image plane of an optical system, formed from a point source object. The more punctual the PSF, the better the optical quality. This PSF, which is in the spatial domain, is very important because converted into the frequency domain it is then the optical transfer function (OTF) which makes it possible to simulate the image of any object seen through the lens of the system studied.

It is expressed as follows:

$$OTF(\omega_x, \omega_y) = \int\int_{-\infty}^{+\infty} PSF(x, y) e^{i(x\omega_x + y\omega_y)} dx\, dy$$
$$= \mathrm{Re}(OTF(\omega_x, \omega_y)) + i\, \mathrm{Im}(OTF(\omega_x, \omega_y))$$

Where $\omega_x, \omega_y$ represents the spatial frequencies in Fourier space, x, y the spatial dimensions in real space and Re and Im the real and imaginary parts of a complex number, i being the square root of −1 in complex number space.

The modulation transfer function is the modulus of the optical transfer function, i.e., the square root of its real and imaginary parts to the power of 2.

It is expressed as follows:

$$MTF(\omega_x,\omega_y) = \sqrt{\mathrm{Re}(OTF(\omega_x,\omega_y))^2 + \mathrm{Im}(OTF(\omega_x,\omega_y))^2}$$

The phase transfer function PTF is the argument of the optical transfer function. It is expressed as follows:

$$OTF(\omega_x,\omega_y) = MTF(\omega_x,\omega_y) e^{-iPTF(\omega^x,\omega^y)}$$

To have vision comfort without discontinuity over a wide depth of field, it is useful to think in terms of "phase" and "phase inversion". Indeed, when the MTF-TF becomes null after a peak then has a new peak, this often corresponds to a phase inversion, which means that for a given spatial frequency (100/cycles/mm in the case of an MTF-TF curve at 100/cycles/mm, the perceptible signal is inverted. Thus, for example, a black test pattern on a white background becomes white on a black background.

In the case of IOLs, one can have a phase inversion for high frequencies, but also as a function of defocusing. Thus, for commercial trifocal implants, between intermediate vision and near vision, the implant is no longer sufficiently focused and there is a phase inversion.

Figure 1:
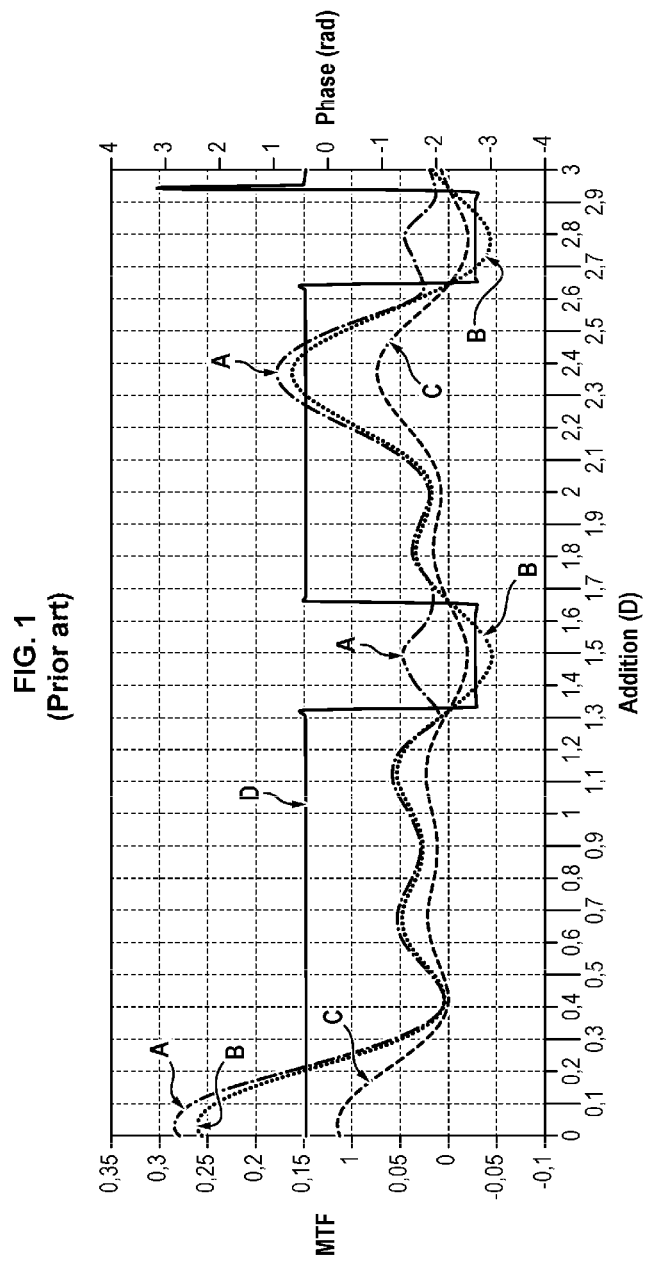
FIG. 1 is an MTF-TF curve of a commercial trifocal implant.

This is the case for FIG. 1 in which we are dealing with a commercial trifocal implant.

In this figure, the x-axis shows addition (from 0 to 3 D in the corneal plane) and the y-axis shows the MTF (left) and the phase (right).

The following curves are plotted:
curve A: MTF curve;
curve B: real part of the OTF curve;
curve C: imaginary part of the OTF curve;
curve D: phase transfer curve.

Unless expressly stated, the figures below repeat the same parameters.

A phase inversion is actually observed around addition 1.5 D (in the corneal plane). This implant therefore does not allow sharp and continuous vision with no phase inversion between intermediate vision and near vision.

Definition of the Parameters Referred to in the Present Invention

The MTF-TF (or TFMTF="through focus modulation transfer function") represent the optical quality (in % or ratio between 0 and 1) of contrast of the image for a starting object having a contrast of 100%) as a function of the viewing distance (described by addition in dioptres: 0 D=distance vision/+1 to +2 D=intermediate addition/3 D=near addition in the corneal plane).

These are curves simulated with optical simulation software such as that known by the brand name Zemax for intraocular implants placed in an average eye model.

An MTF-TF curve is established for a given spatial frequency. Usually, for multifocal implants, we are interested in the MTF-TF at 50 cycles/mm. MTF-TF at 25 cycles/mm (larger objects) and 100 cycles/mm (smaller objects) are also interesting.

An MTF-TF curve at 50 cycles/mm (for example) of a given optical profile depends on the pupil of the optical system and the wavelength of the light used.

Thus, we are preferably interested in a green wavelength (546 nm) but it can also be interesting to plot the photopic MTF-TF corresponding to the integral of the wavelengths of daylight, as well as scotopic MTF-TF (night vision).

Likewise, we are preferably interested in a pupil of 3 mm diameter (corresponding to a well-lit vision (reading in day vision), but the continuity of MTF-TF can be interesting for pupils of 2 to 6 mm.

An MTF value greater than 0.15 is considered as providing a satisfactory near vision to the wearer.

Near vision, NV, is typically equal to +3 D (in corneal plane addition), but can be comprised between +2 D and +4 D.

Intermediate vision, IV, is typically equal to +1.5 D (in corneal plane addition), but can be comprised between +1 D and +2 D.

Implants According to the Invention

The enlarged near vision implants at constant phase according to the invention can be defined as follows:

These are diffractive implants possessing distance vision and near vision whose optical transfer function phase is constant over an enlarged intermediate to near vision zone, i.e., with no phase inversion up to a spatial frequency of 100 cycles/mm, this optical transfer function being constant over an addition value range which is at least 30% (and preferably 45%) larger than that of a conventional bifocal implant, such as the one named ARtis PL M, sold by the present applicant.

Figure 2:
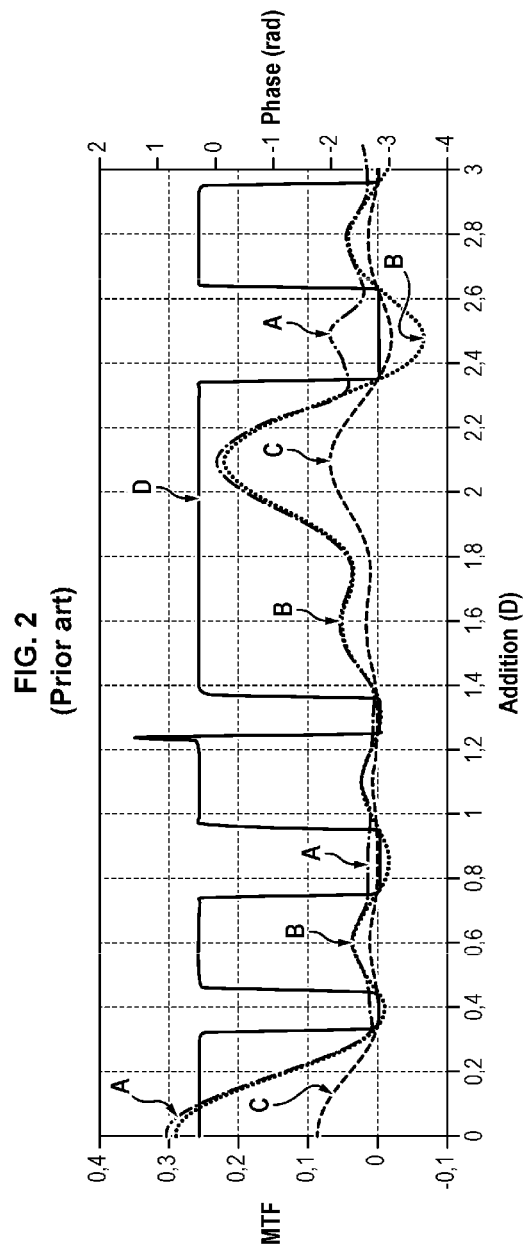
FIG. 2 is an MTF-TF curve of a commercial bifocal implant.

FIG. 2 attached shows the phase transfer function at 100 cycles/mm according to the addition for a conventional bifocal implant of addition +3 D.

Note that the phase is constant (curve D) over the 1.35 D to 2.35 D zone, or a depth of 1 D in the corneal plane.

Figure 3:
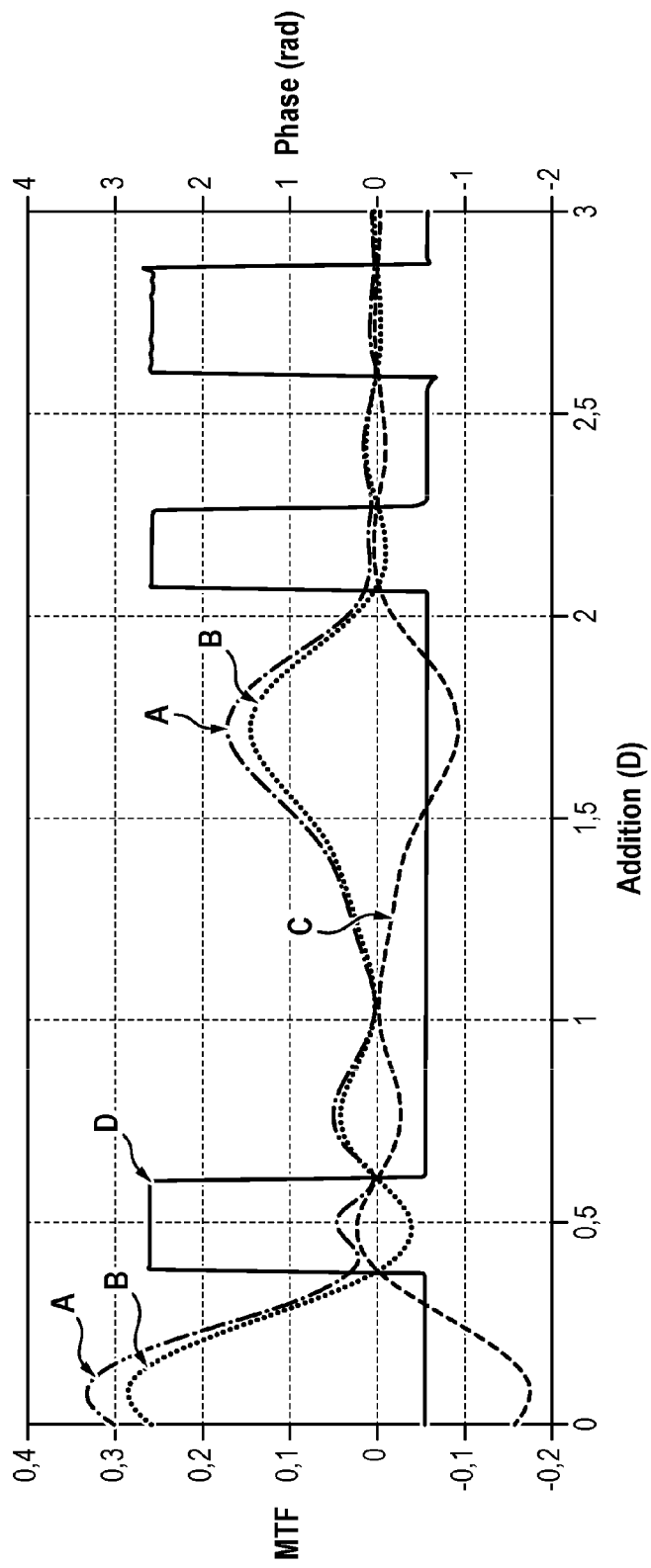
FIG. 3 is an MTF-TF curve of an implant according to the invention.

An example of enlarged near vision profile at constant phase of an implant according to the invention is shown in FIG. 3.

Note that the phase is constant over the 0.6 D to 2.05 D zone, or a depth of 1.45 D in the corneal plane.

Such curves can be obtained from different diffractive optical implants, which will be described below.

It is obviously considered that an implant of this type comprises a body with at least one optical surface having an optical axis and a plurality of diffractive zones arranged concentrically around this optical axis, these concentric zones each having at least one radius r.

For a bifocal implant, the radii of successive rings have for radius rN such that:

$$r_N = \sqrt{2N\lambda \cdot f_p}$$

relation wherein:
N is the ring number (counting from the centre);
$f_p$ is the focal length corresponding to the addition for near vision
$\lambda$ is the design wavelength (typically 546 nm).

Height h of the diffractive steps (echelettes) of the zones equals:

$$h = \alpha \frac{\lambda}{\Delta n}$$

relation wherein:
$\Delta n$ is the refractive index variation (i.e., the difference between the refractive index of the implant material and that of the aqueous humor of the eye or the surrounding environment when it is a question of an intracorneal implant);
$\alpha$ is the height factor of the profile.

If $\alpha = 0.5$, then the relative energy distribution is 50% for distance vision and 50% for near vision.

The shape of the diffractive echelettes of each zone is called "kinoform" and is described by a parabola on each echelette such that:

$$\text{Profile}(x) = \alpha \cdot \frac{\lambda}{\Delta n} \cdot \frac{r_N^2 - x^2}{r_N^2 - r_{N-1}^2}$$

Where x is tne radial position.

According to the invention, an implant having a continuous phase profile between near vision and intermediate vision is created by making use of diffractive profiles giving an extended depth of field.

The central area of such an implant is defined by a profile for which the radius of successive rings rN is fixed by an equation of the type:

$$r_N = \sqrt{2N\lambda f_p + 2 \cdot \lambda \cdot F2(N) \cdot \Delta_f}$$

expression in which F2(N) is a polynomial of the variable N of minimum order 3. F2(N) can have as expression $$F2(N) = cte + a \cdot N + b \cdot N^2 + c \cdot N^3 + d \cdot N^4 + \ldots$$

where:
N is a whole number greater than 1;
$\lambda$ is the conception wavelength;
$f_p$ is the focal length corresponding to the addition for near vision
$\Delta_f$ is the focal length variation;
cte is a constant consisting of a real number comprised between −5 and +5,
a, b, c, and d are real numbers comprised between −5 and +5, Note that F2(N) can be a function whose limited development or Taylor is equivalent to the polynomial expressed above. The term "equivalent" means that the limited development or Taylor of said function gives the same results as the F2(N) function expressed above.

Purely by way of indication, these implants can comprise a central region (for example of diameter 1.5 to 6 mm) with an extended depth of field and optionally a "peripheral" zone region that can be described as conventional (for example, from 2 to 6 mm diameter).

Figure 4:
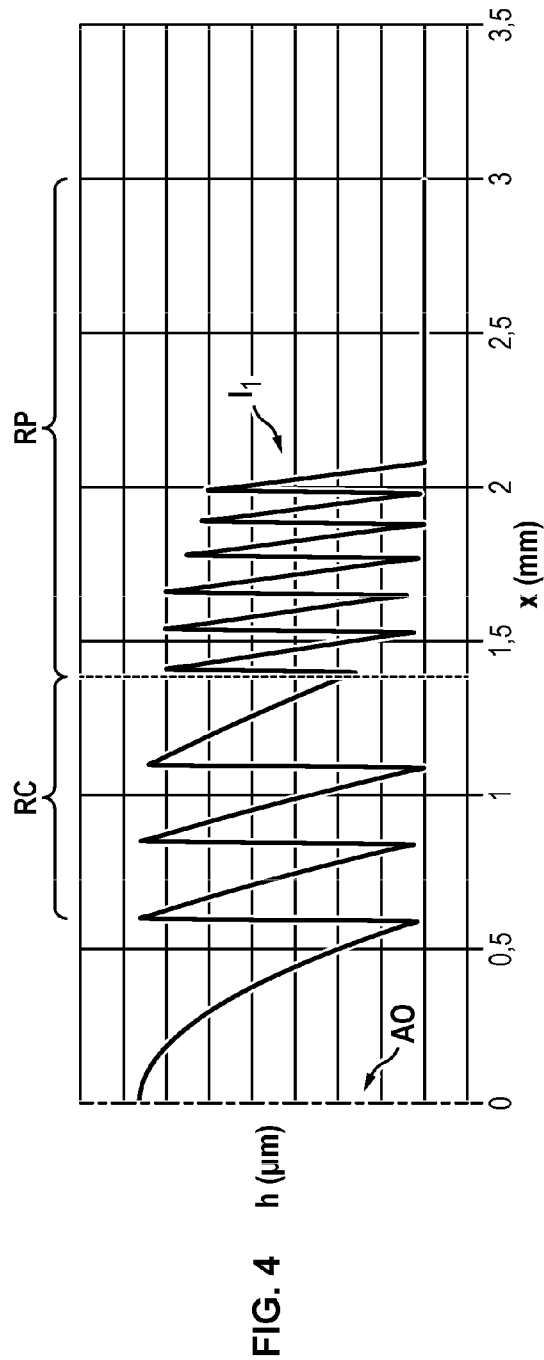
FIG. 4 is a half-profile view of an implant according to the invention, it being understood that in this figure, the variability of the echelettes represented is due to an apodization.

FIG. 4 shows the "half" profile of an implant I1 according to the present invention.

"Half" profile means the fact that the y-axis, which reflects the height of the echelettes of these implants in micrometers, coincides with their optical axis AO and that only the profile which extends on one side of this axis has been shown.

In this figure, said central and peripheral regions are respectively referenced RC and RP.

Note here that the profile of the fourth echelette visible in this figure has been cut, due to the start of the peripheral region RP.

Although "kinoform", the echelettes may have a different shape (sine or cosine, for example), this different shape not drastically modifying the present invention.

In the case presented here, the different refractive zones have a circular contour. However, according to alternative embodiments, not shown here, these diffractive zones have an elliptical contour of which rN is the small radius.

Still according to the embodiment presented here, the central region RC has an extended depth of field, has a radius of at least one millimeter and is surrounded by a peripheral region RP which is refractive or diffractive, monofocal or multifocal, for example with a bifocal equation:

$$r_N = \sqrt{2N\lambda \cdot f_p},$$

Conversely, this could be the reverse, so that it would be the central region RC, having a radius of at least one millimeter, which would be refractive or diffractive, monofocal or multifocal, for example with a bifocal equation:

$$r_N = \sqrt{2N\lambda \cdot f_p}$$

Figure 5:
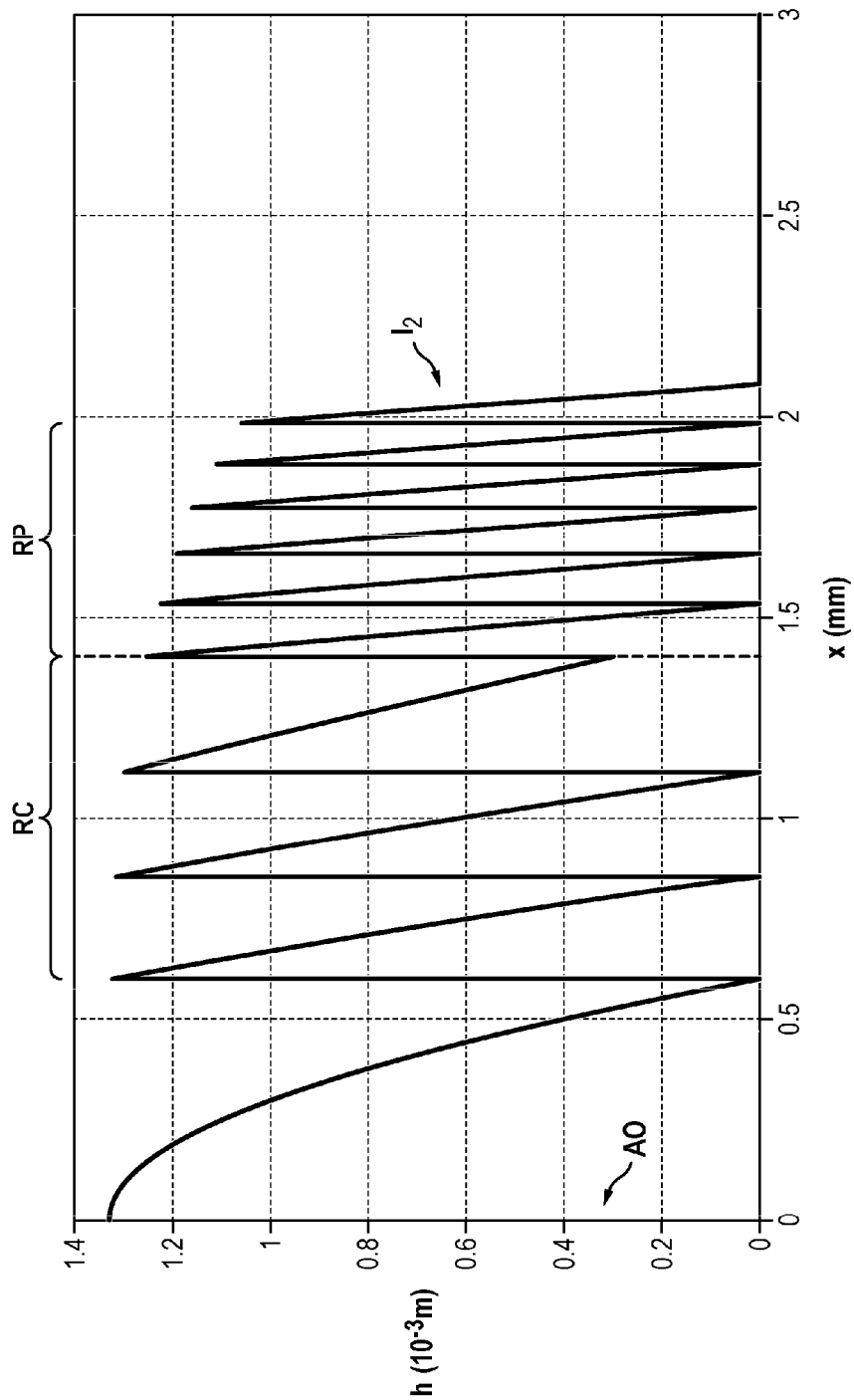
FIG. 5 is a half-profile view of an implant according to the invention, it being understood that in this figure, the variability of the echelettes represented is due to an apodization.

FIG. 5 shows the "half-profile" of another implant I2 according to the present invention.

The main parameters for implants according to the invention are given below.

Example 1

Function F(N) of order 4 (which corresponds to the profile of FIG. 5 and to the curves of FIG. 6):

TABLE 1

| Central region: | $f_{p1}$ | 1000/3.05 |
|---|---|---|
| rings 1 to 4 | $\propto_1$ | 0.5 |
| | $\Delta_f$ | 800 |
| Peripheral region: | $f_{p2}$ | 1000/2.77 |
| rings 6 to 12 | $\propto_2$ | 0.5 |

Central region:

$$r1_N = \sqrt{2\,\lambda \cdot N \cdot f_{p1} + 2\,\lambda \cdot \left(N \cdot \left(\frac{N-1}{5}\right)^3\right) \cdot \Delta_f}$$

$$\text{Profile}_1(x) = \propto_1 \cdot \frac{\lambda}{\Delta n} \cdot \frac{r1_N^2 - x^2}{r1_N^2 - r1_{N-1}^2}$$

Peripheral region:

$$r2_N = \sqrt{2\,(N)\,\lambda \cdot (f_{p2})}$$

$$\text{Profile}_2(x) = \propto_2 \cdot \frac{\lambda}{\Delta n} \cdot \frac{r2_N^2 - x^2}{r2_N^2 - r2_{N-1}^2}$$

Figure 6:
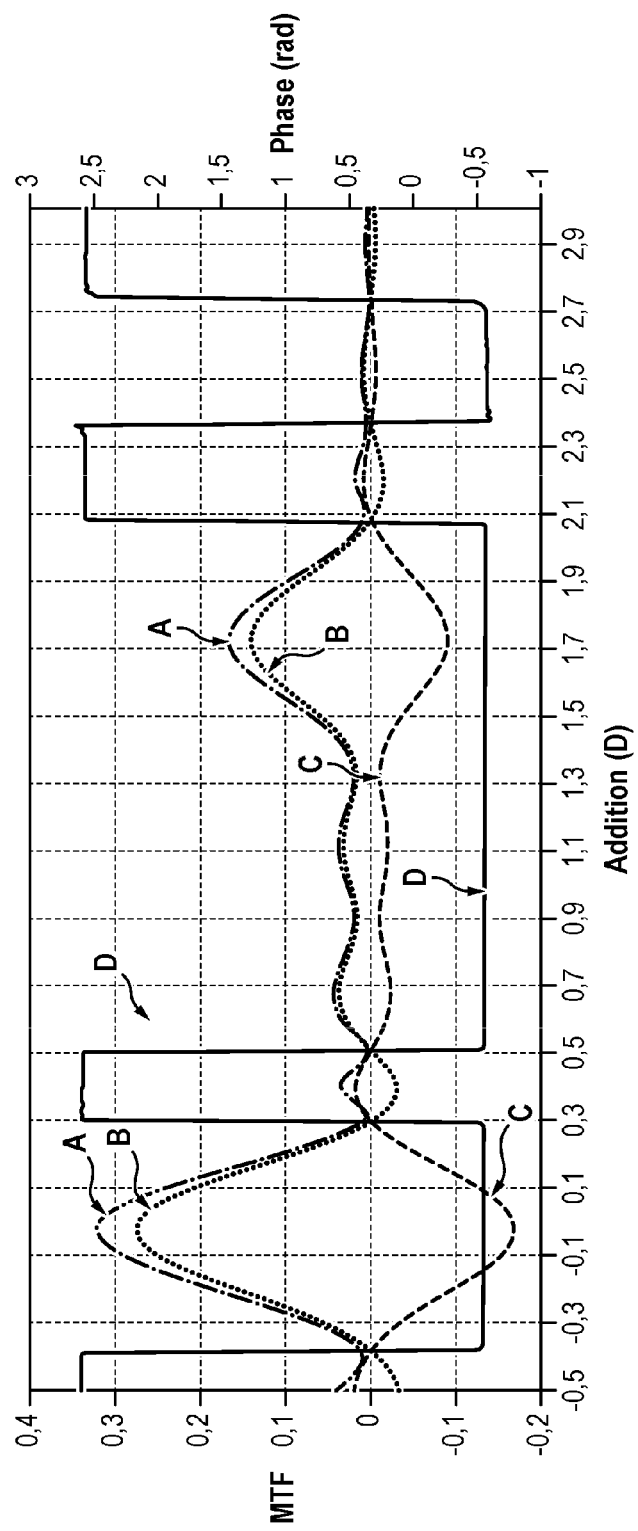
FIG. 6 is an MTF-TF curve of an implant according to the invention.

Thus it is observed in FIG. 6 that the phase is constant over the 0.5 D to 2.05 D zone, or a depth of 1.55 D in the corneal plane.

Figure 7:
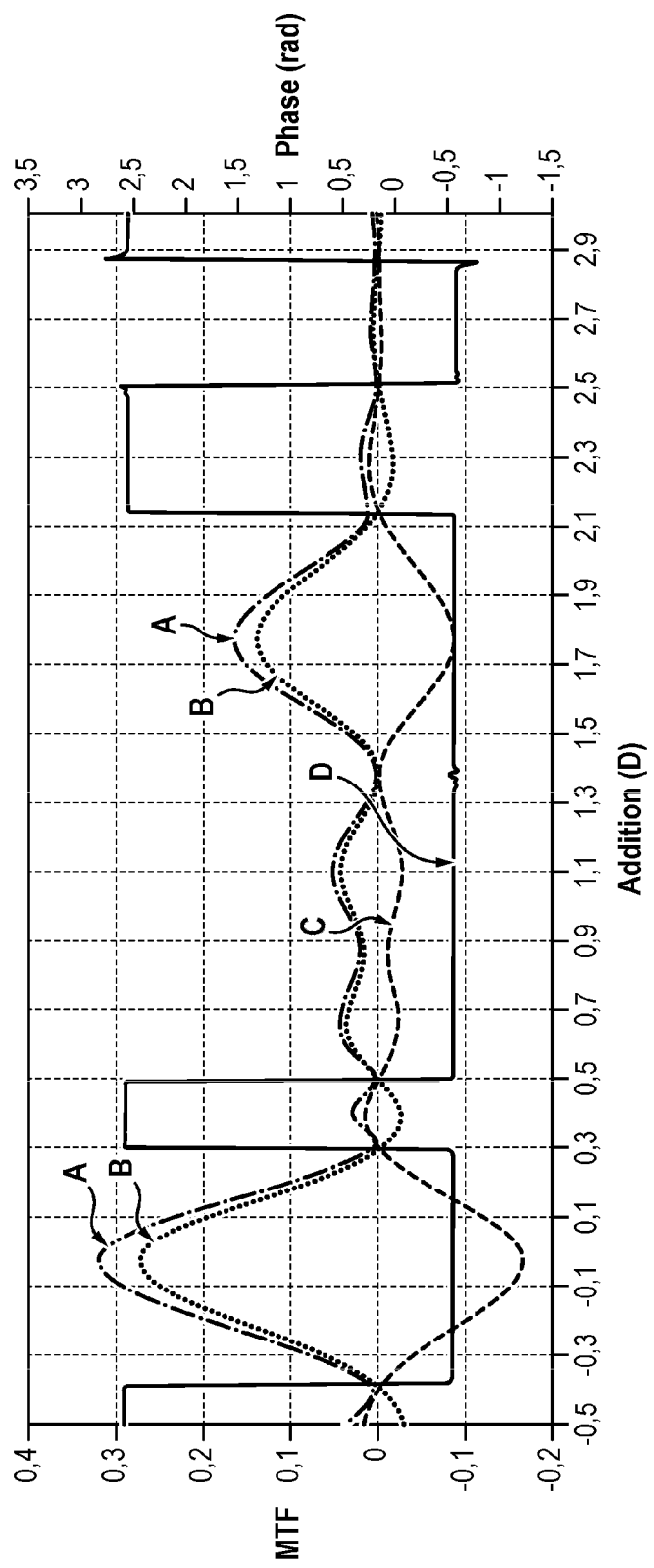
FIG. 7 is an MTF-TF curve of an implant according to the invention.

Example 2 (Which Corresponds to the Profile of FIG. 4 and to the Curves of FIG. 7)

Function F(N) of order 5:

TABLE 2

| Central region: | $f_{p1}$ | 1000/3.05 |
|---|---|---|
| rings 1 to 4 | $\propto_1$ | 0.5 |
| | $\Delta_f$ | 1400 |
| Peripheral region | $f_{p2}$ | 1000/2.77 |
| rings 6 to 12 | $\propto_2$ | 0.5 | central region:

$$r1_N = \sqrt{2\,\lambda \cdot N \cdot f_{p1} + 2\,\lambda \cdot \left(N \cdot \left(\frac{N-1}{5}\right)^4\right) \cdot \Delta_f}$$

$$\text{Profile}_1(x) = \propto_1 \cdot \frac{\lambda}{\Delta n} \cdot \frac{r1_N^2 - x^2}{r1_N^2 - r1_{N-1}^2}$$

peripheral region:

$$r2_N = \sqrt{2\,(N)\,\lambda \cdot (f_{p2})}$$

$$\text{Profile}_2(x) = \propto_2 \cdot \frac{\lambda}{\Delta n} \cdot \frac{r2_N^2 - x^2}{r2_N^2 - r2_{N-1}^2}$$

Thus it is observed in FIG. 7 that the phase is constant over the 0.5 D to 2.14 D zone, or a depth of 1.64 D in the corneal plane.

Figure 8:
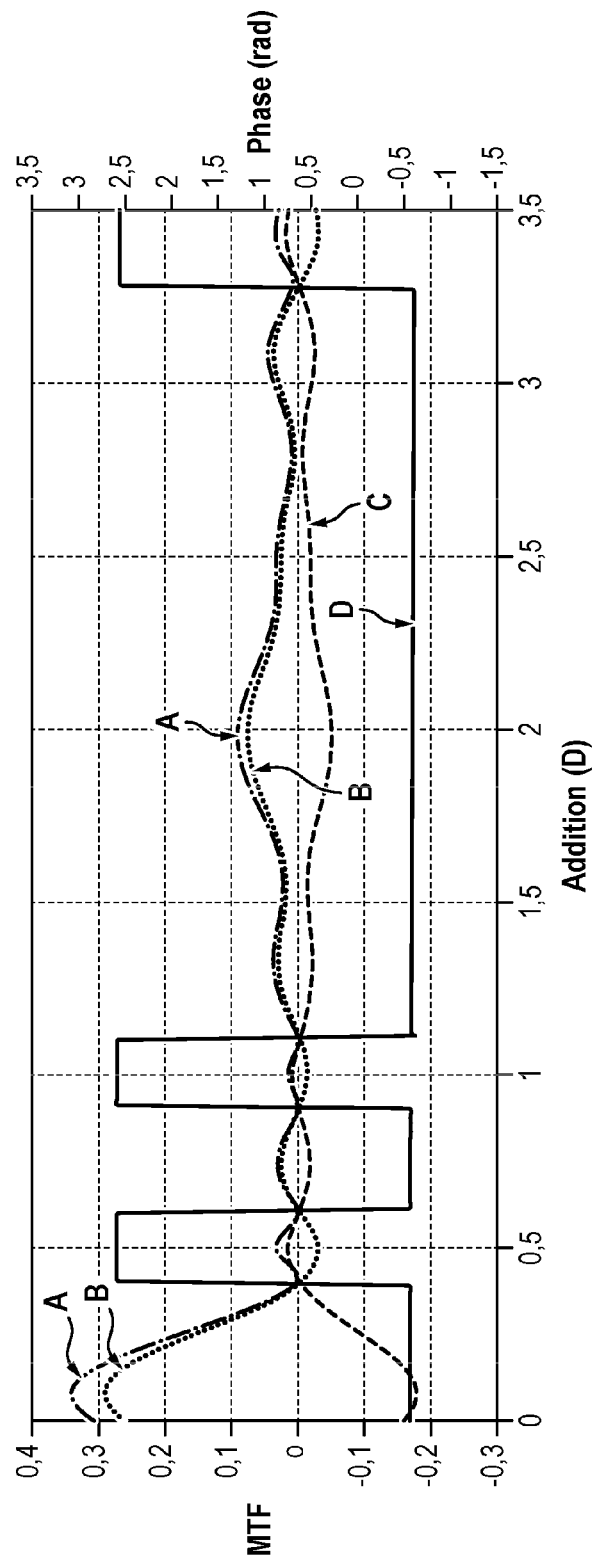
FIG. 8 is an MTF-TF curve of an implant according to the invention.

Finally, in the embodiment of FIG. 8, the phase is constant over the 1.1 D to 3.3 D zone, or a depth of 2.2 in the corneal plane.

As indicated above, the diffractive profiles (also called steps or echelettes) of the implants according to the invention can be apodized (i.e., we are dealing with a reduction in the height of the steps between the centre and the periphery) as a function of the radius (which constitutes variable x), according to the following equation:

Apodized Profile(x)=Profile(x)*Apodization(x)

The "apodization (x)" function is a decreasing function such that, for 0<abs(x)<r max (r max=maximum radius of the diffractive profile), then 0 <Apodization (x)≤1.

For example, this function can take the following form: Apodization(x)=(1−abs(a·x/b)^c) with a, b and c consisting of real numbers.

The diffraction profile can be composed of concentric, circular or oval diffractive steps (echelettes). In other embodiments, the diffractive effect can be obtained by alternating full zones and empty zones (holes, slits), which modifies the local refractive index by zones and generates diffraction in the same way as the echelettes.

Expressed differently, this diffractive profile can be defined not by a geometric shape, but by a variation of refractive indices of the material(s) that compose it and which will create the same effect. The modification of the refractive index, for example, can be obtained by alternating full zones "n mat" and empty zones "n0" (made up of holes or slits), which modifies the local refractive index by zones and generates diffraction in the same way as the echelettes.

The implants according to the invention make it possible to correct presbyopia. They can also correct other ametropias (myopia, hyperopia, astigmatism).

These may be intracorneal implants (lenticles), anterior chamber (phakic or pseudophakic), or posterior intraocular chamber or sulcus implants).

The invention claimed is:

1. A diffractive intraocular implant with correct distance vision, i.e., a vision such that the modulation transfer function (MTF) of said implant is greater than 20% at 50 cycles/mm in a pupil of 3 mm in diameter, and with enlarged near vision, i.e., an absence of discontinuity of its phase transfer curve as a function of viewing distance, wherein said implant:

has a phase transfer curve as a function of the viewing distance with an absence of discontinuity over a depth of field of at least 1.3 D in the corneal plane, i.e., over an area of additions in the corneal plane of at least 1.3 D, the addition in the corneal plane being understood as the inverse of the distance between the object viewed and the cornea, which absence of discontinuity is located between intermediate vision and near vision, i.e., between 0.5 D and 4 D for spatial frequencies from 0 to 100 cycles/mm for a pupil of at least 3 mm in diameter;

comprises a body with at least one optical surface having an optical axis and a plurality of diffractive zones arranged concentrically around said optical axis, said concentric diffractive zones each having at least one radius r and being distributed between a central region and a peripheral region, at least one central region or peripheral region of said diffractive zones having a profile of N successive echelettes, successive radii $r_N$ of which, as one moves away from said optical axis, respond to the relation:

$$r_N = \sqrt{2N\lambda f_p + 2 \cdot \lambda \cdot F2(N) \cdot \Delta_f}$$

wherein:

N is a whole number greater than 1;

λ is the conception wavelength;

$f_p$ is the focal length corresponding to the addition for near vision;

$\Delta_f$ is the focal length variation, which is not zero, positive or negative, and whose absolute value is less than 10,000;

F2(N) is a polynomial of the variable N of order comprised between 3 and 5, which is expressed as follows:

$$F2(N) = cte + a \cdot N + b \cdot N^2 + c \cdot N^3 + d \cdot N^4 + \ldots$$

and wherein the maximum height of said successive echelettes, i.e., diffractive steps, namely the difference between two successive echelettes, is given by the relation:

$$h = \alpha \frac{\lambda}{\Delta n}$$

wherein:

$\Delta n$ is the refractive index variation, i.e., the difference between the refractive index of the implant material and that of the aqueous humor of the eye or the surrounding environment;

α is the height factor of the echelette, comprised between 0.25 and 1.75, wherein the intraocular implant is one of an anterior chamber intraocular lens (IOL) or a posterior chamber intraocular lens (IOL).

2. The implant according to claim 1, wherein "cte" is a real number comprised between −5 and +5.

3. The implant according to claim 1, wherein a, b, c, d, etc. are real numbers comprised between −5 and +5.

4. The implant according to claim 1, wherein said diffractive zones have a circular contour.

5. The implant according to claim 1, wherein said diffractive zones have an elliptical contour of which $r_N$ is the small radius.

6. The implant according to claim 1, wherein said diffractive zones are made up by alternating full zones and empty zones, said empty zones consisting of slits or of holes.

7. The implant according to claim 1, wherein said phase transfer curve has no discontinuity from 0.8 D in the corneal plane.

8. The implant according to claim 1, wherein said phase transfer curve has no discontinuity from 2 D in the corneal plane.

9. The implant according to claim 1, wherein the central region has a radius of at least one millimeter and is surrounded by a peripheral region which is refractive or diffractive, monofocal or multifocal.

10. The implant according to claim 1, wherein F2(N) is a polynomial of the variable N of order 3.

11. The implant according to claim 1, wherein the optical surface comprises an aspherical surface.

12. The implant according to claim 1, wherein the optical surface has an apodized profile, i.e., the height of said echelettes decreases as one moves away from said optical axis, in order to limit the halo phenomenon in night vision.

* * * * *